US009552958B2

(12) United States Patent
Hooghan

(10) Patent No.: US 9,552,958 B2
(45) Date of Patent: Jan. 24, 2017

(54) ALIGNMENT MARKING FOR ROCK SAMPLE ANALYSIS

(71) Applicant: Weatherford/Lamb, Inc., Houston, TX (US)

(72) Inventor: Kultaransingh N. Hooghan, Houston, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 0 days.

(21) Appl. No.: 14/189,506

(22) Filed: Feb. 25, 2014

(65) Prior Publication Data

US 2015/0243471 A1 Aug. 27, 2015

(51) Int. Cl.
| | |
|---|---|
| *H01J 37/20* | (2006.01) |
| *H01J 37/28* | (2006.01) |
| *G01N 23/225* | (2006.01) |
| *G01N 1/32* | (2006.01) |

(52) U.S. Cl.
CPC ............... *H01J 37/20* (2013.01); *G01N 1/32* (2013.01); *G01N 23/2251* (2013.01); *G01N 23/2255* (2013.01); *H01J 37/28* (2013.01); *G01N 2223/616* (2013.01); *H01J 2237/08* (2013.01); *H01J 2237/202* (2013.01); *H01J 2237/3174* (2013.01); *H01J 2237/31749* (2013.01)

(58) Field of Classification Search
USPC ........................................... 250/492.1, 491.1
See application file for complete search history.

(56) References Cited

U.S. PATENT DOCUMENTS

| | | | |
|---|---|---|---|
| 4,311,546 A * | 1/1982 | Abe et al. ...................... 438/507 |
| 6,153,492 A | 11/2000 | Wege et al. | |
| 6,975,040 B2 | 12/2005 | Dower et al. | |
| 2013/0143412 A1 | 6/2013 | Moriarty et al. | |
| 2014/0139608 A1* | 5/2014 | Rosario ............. B23K 26/0006 347/225 |

OTHER PUBLICATIONS

Willford, K.H., "A Guide to SIMS Targeting in Difficult Samples," Department of Geosciences University of Wisconsin-Madison, dated 2012, obtained from http://www.geology.wisc.edu/~wiscsims/pdfs/sims_targeting.pdf on Feb. 24, 2014.
Giannuzzi, L. et al., "Introduction to Focused ION Beams," Chapter 5 entitled "Device Edits and Modifications" by Kultaransingh (Bobby) N. Hooghan, Springer Science+Business Media, Inc., pp. 87-106, copyright 2005.
Int'l. Search Report and Written Opinion in counterpart PCT Appl. PCT/US2015/016115, dated May 11, 2015.
Wirth, et al., "Focused Ion Beam (FIB) combined with SEM and TEM," Chemical Geology, vol. 261, No. 3-4, Apr. 30, 2009, pp. 217-229.
Uchic, et al., "Three-Dimensional Microstructural Characterization Using Focused Ion Beam Tomography," MRS Bulletin, vol. 32, No. 05, May 1, 2007, pp. 408-416.

* cited by examiner

*Primary Examiner* — Kiet T Nguyen
(74) *Attorney, Agent, or Firm* — Blank Rome LLP

(57) ABSTRACT

A method for using a Focused Ion Beam and/or Scanning Electron Microscope (FIB/SEM) for etching one or more alignment markers on a rock sample, the one or more alignment markers being etched on the rock sample using the FIB/SEM. The one or more alignment markers may further be deposited with a platinum alloy or other suitable compositions for increasing alignment marker visibility.

24 Claims, 5 Drawing Sheets

ALIGNMENT MARKING FOR ROCK SAMPLE ANALYSIS

BACKGROUND OF THE DISCLOSURE

In the oil and gas industry, rock samples are routinely collected and analyzed for determining geophysical properties downhole. Historically, those skilled in the art have only looked at features inherently present on the surface of rock samples for referencing specific sites to be analyzed. The inherent features are used to reference each point/location on the samples. Although this process of locating features on the surface of the rock samples using an optical inspection of the features of the rock sample itself may be repeatable, this process is greatly undesired because of the amount time involved in having to re-align the exact location of the specific site to be analyzed.

As can be imagined, there are other issues that can arise from having to re-align the specific site for analysis by using only optical inspection, especially after a rock sample has been removed from a tester and later reinserted. Further, some rock samples are heated during the testing process. Heating the samples may sometimes change the topography of the samples, making it almost impossible to optically locate and re-align the specific site to be analyzed.

Locating microscopic features on a surface has been needed in other fields, such as semiconductor fabrication. For example, it is known in the art of semiconductor fabrication to induce a top passivation layer of a semiconductor chip with alignment marks for forming induced topographical features that are used for more easily locating selective areas of the chip. For example, FIG. 1 illustrates a semiconductor chip 100 having alignment markers 10 according to the prior art. As shown in the illustration, the alignment markers 10 have been formed so that each mark 10 is aligned with a particular edge of the chip 20.

The purpose for inducing these alignment markers 10 on the semiconductor chip 100 is so that the chip 100 may be more readily aligned for analysis and testing. In other words, by using the alignment markers 10, the chip 100 may be quickly and accurately positioned for testing. As shown, the alignment markers 10 also include a rectangular or square portion 15 near each mark 10. These portions 15 serve to indicate which quadrant the chip 100 lies (i.e., the chip's directional orientation). Alignment markers 10 related to semiconductor chips are detailed in U.S. Pat. No. 6,975,040, which is incorporated herein in its entirety.

Semiconductor chips normally have a planned mapping of recognizable properties, making it conducive to finding features of interest on the chip. For example, when finding features of semiconductor chips, there are still some distinguishable areas of the chip that can be identified (e.g., known metal areas on the chip, through which bonding pads may provide electrical contact with other conductive surfaces). Furthermore, any markings on semiconductor chips are produced during the fabrication process. These prefabricated marking then allow the chip to be aligned later for analysis based on mapped information in a database for the chip.

On the other hand, rock samples are completely unmapped, having an utterly random surface and a complete natural distribution of topographical features. Thus, rock samples are typically completely indistinguishable. For this reason, existing visual distinctions have always been used in locating regions of interest on rock samples.

Because the current method of locating and re-aligning specific sites on rock samples by optically inspecting inherent features of the rock samples is inefficient and can cause inconsistencies during sample analysis, and because rock samples do not undergo a fabrication process where alignment markers can be introduced, it is desirable to have a process for introducing marks on a rock sample for quickly and repeatedly establishing the exact location of the specific site to be analyzed. The subject matter of the present disclosure is directed to overcoming, or at least reducing the effects of, one or more of the problems set forth above.

SUMMARY OF THE DISCLOSURE

To achieve the above, as well as other related embodiments, the subject matter of the present disclosure is dedicated to a method for using a Focused Ion Beam and/or Scanning Electron Microscopy (FIB/SEM) for etching one or more alignment markers on a rock sample, the one or more alignment markers being etched using the FIB. The foregoing summary is not intended to summarize each potential embodiment or every aspect of the present disclosure.

DETAILED DESCRIPTION OF THE DISCLOSURE

Techniques are disclosed for marking rock samples so operators of an analysis device can carry out site specific analysis of the samples. The techniques make the analysis a repeatable process. The techniques can typically be used for analytical services on polished rock samples using a variety of analysis devices, namely imaging devices, optical microscopes, Secondary Ion Mass Spectrometry (SIMS), Focused Ion Beam/Scanning Electron Microscope (FIB/SEM), Cathodoluminescence (SEM-CL), etc. The marking techniques are especially useful after the sample is removed from an analysis device, after part of the analysis is complete, and later reinserted to complete further analysis.

In the disclosed techniques, a Focused Ion Beam/Scanning Electron Microscope (FIB/SEM) introduces alignment markers to bracket, outline, delineate, etc. a region of interest on the rock sample's surface and/or to bracket, outline, delineate, etc. an entire sample (sometimes in the realm of a 1-in round/square). Using the alignment markers, operators can then repeatedly re-align the sample to the region of interest to go back to the previously marked regions during stages of the analysis. The alignment markers can include (a) milled locations, (b) deposition locations, or (c) a combination of both milled and deposition locations. Either way, the alignment markers allow operators to triangulate points on the rock sample's surface and mark regions of interest so those regions can be readily relocated as more analysis is performed.

Figure 1:
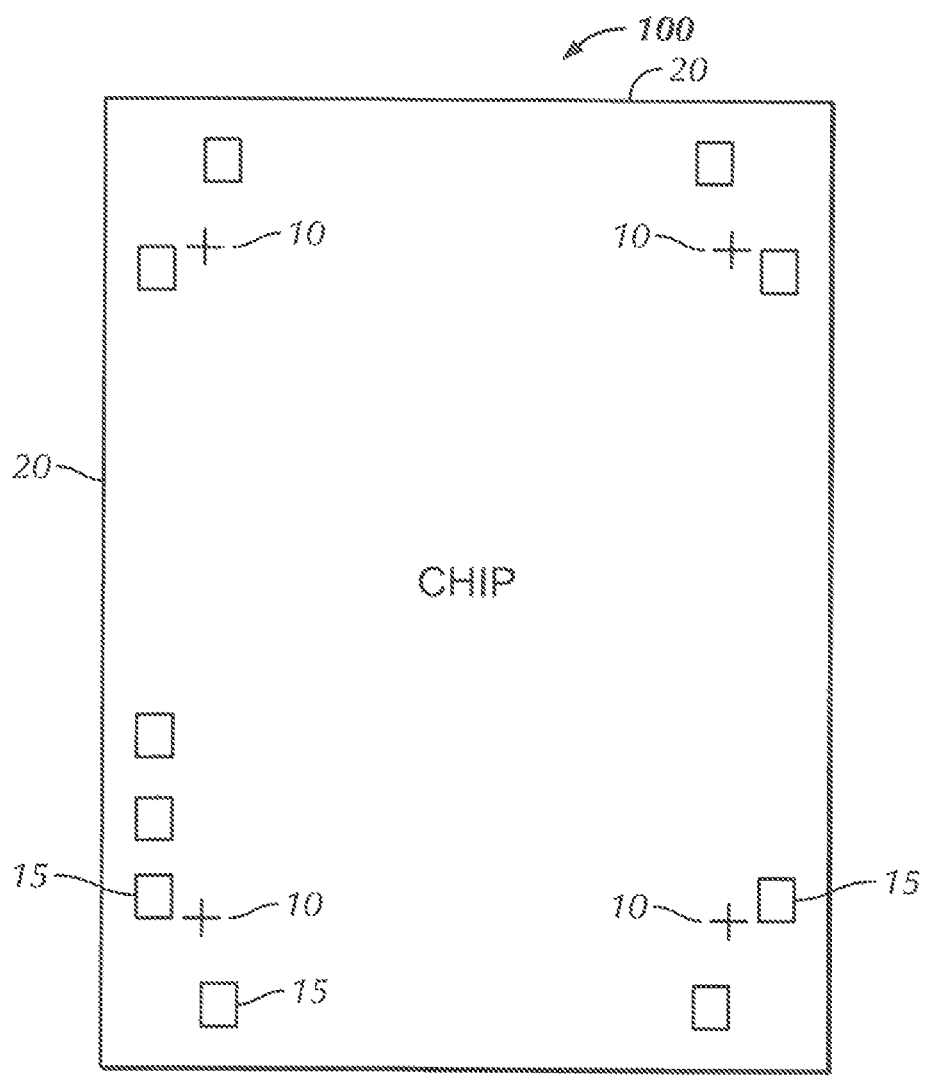
FIG. 1 illustrates a semiconductor chip having alignment markers according to the prior art.
Figures 2A, 2B:
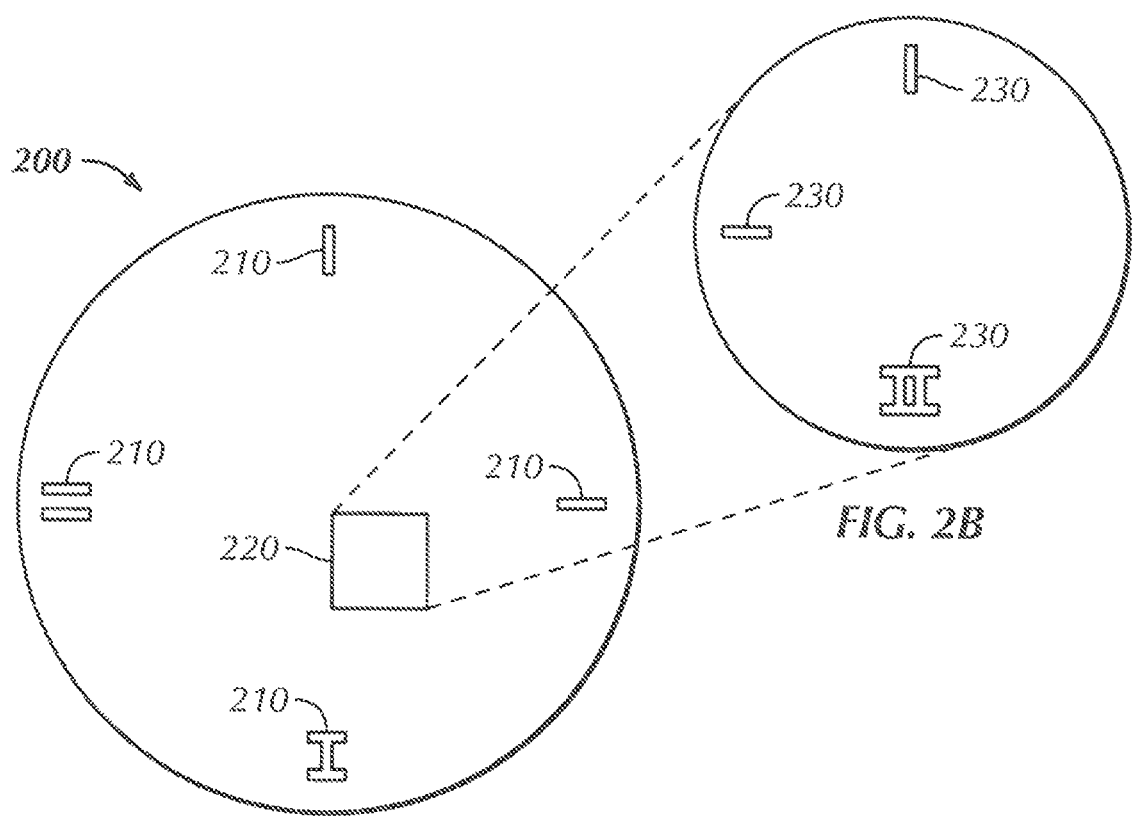
FIG. 2A illustrates a global view of a rock sample having been aligned for marking.
FIG. 2B illustrates a microscopic view of a rock sample having been aligned for marking.

Referring now to the figures, FIG. 2A illustrates a surface of a rock sample 200 having global alignment markers 210, and FIG. 2B illustrates a microscopic view of the rock sample 200 having local alignment makers 230. In exploration operations, geologists and others analyze various rock samples, such as the sample 200, to determine characteristics of a downhole formation. In many instances, the geologists want to analyze and image particular features, areas, or regions of the rock sample 200 using analysis devices, such as optical microscopes, Secondary Ion Mass Spectrometry (SIMS), Focused Ion Beam Scanning Electron Microscope (FIB-SEM), Cathodoluminescence (SEM-CL), and the like.

As shown in FIG. 2A, the rock sample 200 as a whole may be globally positioned, and global alignment markers 210 may be introduced globally (i.e., global marking) so that the alignment of the entire sample 200 itself may be quickly and easily aligned and/or re-aligned for analysis. The global markings 210 can be used to locate (via coordinates, grids, triangulation, scaling, etc.) the localized regions of interest, which have their own markings. Conceivably, even intermediate regions of interest can have a form of global or local markings within the global markings 210 and bracketing one or more local regions of interest.

With respect to the local aspect of the present disclosure, a portion the rock sample 200 is shown in FIG. 2B magnified using an optical microscope or other suitable means for magnification. A localized area 20 may be identified for analysis using local alignment markers 230 (i.e., local marking). As shown in FIG. 2B, the localized area 220 of the rock sample 200 can have a round or square area for identifying the specific area to be analyzed. This localized area 220 may range in size, depending upon the level of magnification and the size of the area to be analyzed. As will be appreciated, different imaging techniques can be used to highlight, enhance, define, etc. the natural features of the sample in the sample 200. For example, back scattered imaging, secondary imaging, secondary electron (SE), backscattered electron (BSE), or other imaging techniques may be used in a FIB, SEM, SIMS, or other device to find and show the details of the rock sample 200. Furthermore, after this area has been identified, the localized area 220 may be used as reference for forming the local alignment markers 230.

Also, although the localized area 220 is represented within the rock sample 200 of FIG. 2B, it is not necessary that the localized area 220 be etched or deposited within the rock sample 200 itself. In this aspect, depending on the type of optical scope used, the localized area 20 may be temporarily drawn solely for the purposes of aligning the specific area.

Figure 3:
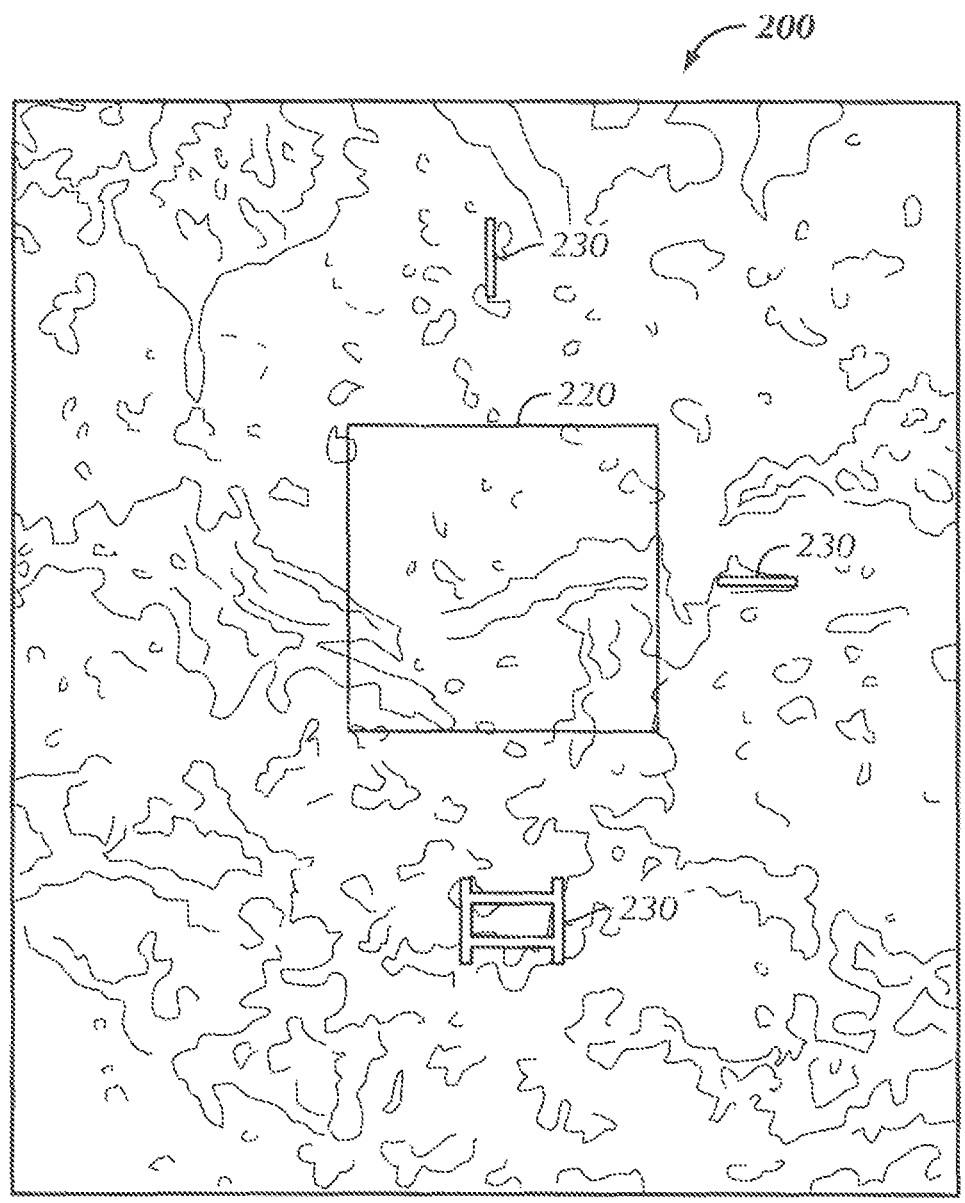
FIG. 3 illustrates a microscopic view of a rock sample having exemplary etched alignment markers.

Referring now to the forming of the alignment markers 210 and 230, FIG. 3 illustrates a microscopic view of a rock sample 200 having exemplary localized alignment markers 230 that have been etched into the surface of the rock sample 200. In this illustration, it is shown that multiple local alignment markers 230 have been formed around the localized area 220 that had been previously identified. Although the positioning of the alignment markers 230 may vary, the alignment markers 230 are positioned at some distance around the local area, to be used later for positioning and alignment of the sample 200. Furthermore, the positioning of the alignment markers 230 may be in any area surrounding the localized area 220, and any distance from the localized area 220.

Furthermore, as shown in FIG. 3, the alignment markers 230 may have differing shapes and orientations. The shapes, sizes, and/or orientation of the alignment markers 230 may vary, and so may the locations of the alignment markers 230 relative to the localized area 220. Alignment marker shapes may include vertical and/or horizontal bars, circles, points, crossed bars, numerals, or any other type of mark or symbol that may be used to identify a location on the rock sample 200.

Using the (FIB/SEM), the alignment markers 230 may be etched or milled into the rock sample 200. Also, for the alignment markers 230 to be etched sufficiently, the depth at which the (FIB/SEM) performs the etching may vary. However, an exemplary depth etched in a rock sample 200 may be between 1 and 3 um. Furthermore, the alignment markers 230 may be filled with a platinum alloy or other material, or the alignment markers 230 may be a combination of etched markers and etched markers that have been filled with platinum or other material. In general, a platinum alloy is preferred due to its visual and metallurgical qualities. Also, although the above description is in reference to localized alignment markers 230, the description also applies to formation of global markers 210.

Figure 4:
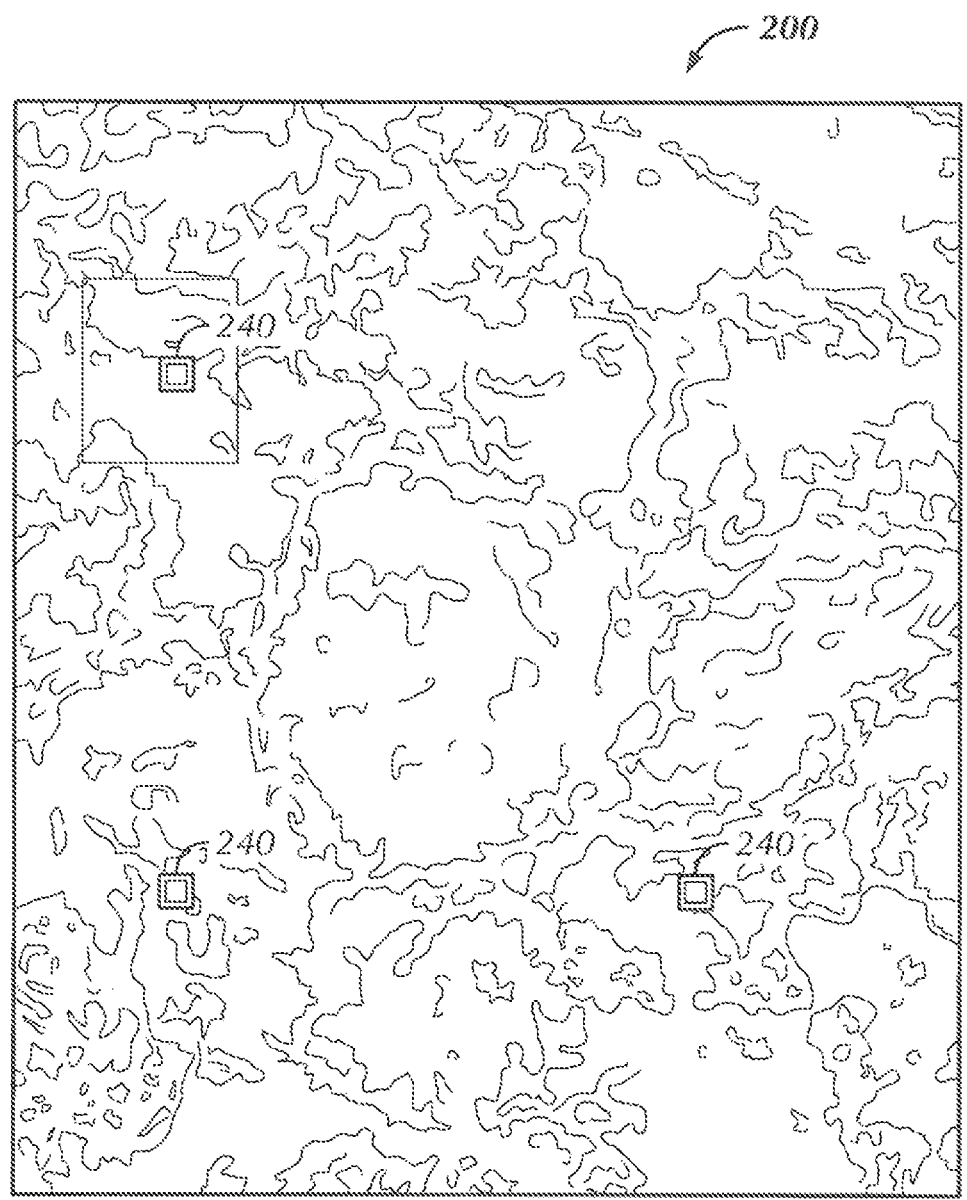
FIG. 4 illustrates a microscopic view of a rock sample having exemplary alignment markers deposited with a platinum alloy.

Square markers may also be etched in the rock sample 200 for alignment purposes. FIG. 4 illustrates a microscopic view of a rock sample 200 having exemplary square markers 240 deposited with a platinum alloy. The formation and use of the square markers 240 is similar to the formation and use of global and local alignment markers 210 and 230, respectively; however, by filling the square markers with a platinum alloy, the square markers may be more easily identified. However, the square nature of the marks are only exemplary, as the global and/or local alignment markers themselves may also be filled.

The process for filling markers with platinum metal involves first milling markers within the local area. As an example, the square marker can have dimensions milled at 15×15×3 um, for example. The markers then may be filled from the bottom with platinum using deposition processes known in the art (i.e., metal deposition, etc.) with a focused ion beam. One purpose for milling the depth of the markers to 3 um is so that the milled location will still be visible if the rock sample 200 is polished. Furthermore, if the alignment marker has been filled with platinum, at least 1 um may be deposited above the surface of the milled location for similar reasons (i.e., polishing the rock sample 200, etc.). Also, although only platinum deposition has been disclosed, other suitable metals or compositions may be deposited within the rock sample 200, considering the depositions allow the relocation and alignment of the local area or global area of the rock sample 200 by being more optically viewable than the milled markers alone.

Figure 5:
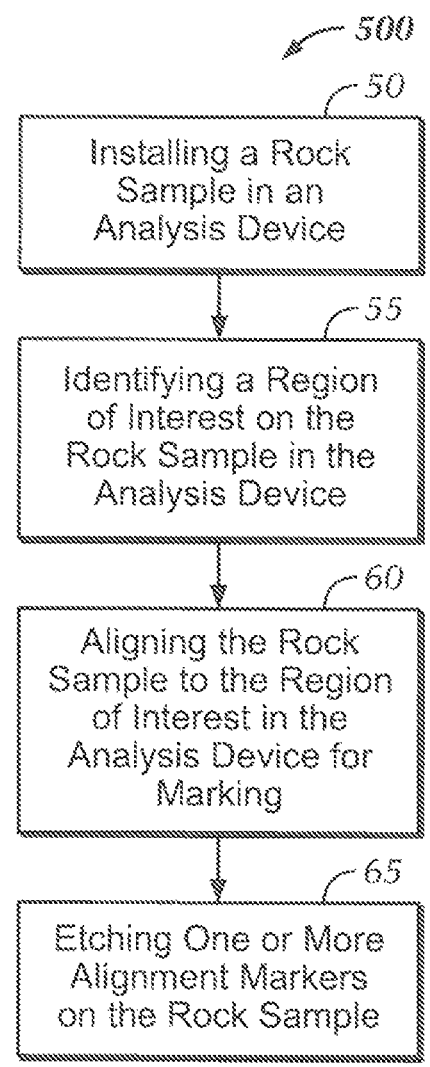
FIG. 5 illustrates an exemplary method for inducing alignment markers for rock samples according to the present disclosure.

Referring now to FIG. 5, an exemplary method for inducing alignment markers 210 and 230 for rock samples 200 is shown according to the present disclosure. As shown, the first step involves identifying a region of interest on the surface of a rock sample 200. Typically, geologists and the like have a particular feature or area on the surface of the rock sample 200 where it is desirable to three-dimensionally image, to determine constituent materials, or to perform some other form of analysis. Operators of an analysis device identify this region of interest on the rock sample 200, and align the rock sample 200 in the analysis device for marking.

As described above, this step may include determining a round or square area for identifying the local area to be analyzed, which may be used as reference for forming the local alignment markers 230. Additionally, optical imaging may be used to identify a region of interest in one device (e.g., optical microscope), which can then be correlated to locating the region of interest in another device (e.g., a Scanning Electron Microscope or other device).

Additionally, as described above, identifying the region of interest and aligning the rock sample 200 in the analysis device for marking may involve globally aligning the sample 200 for global marking first, before locally aligning the sample 200 for localized marking. In this sense, the global marking facilitates locating and aligning to the localized regions 220 bracketed by the localized markers 230.

Aligning rock samples 200 in an analysis device may be performed in any number of ways. One way may include placing or reinserting a rock sample into the device and subsequently moving the rock sample relative to fixed components of the analysis device. However, alignment may also be performed by placing or reinserting the rock sample into the analysis device and subsequently positioning the device's components relative to the rock sample. A combination of these alignment techniques can also be used.

Also, magnification techniques may also be used to align the rock samples. As mentioned above, using an optical microscope or similar device, specific areas of the rock sample may be identified and used for alignment. Furthermore, other techniques including measured scales and triangulation may also be used for alignment. Measured scales typically involves using a grid or scale system relative the topography of the rock sample. By using a scale relative to the topography of such samples, the samples may be more easily mapped and aligned. With the region of interest aligned, the operator uses the analysis device (e.g., FIB/SEM) to etch alignment markers 210 and 230 on the rock sample 200. As noted herein, the alignment markers 210 and 230 may or may not use deposited material, such as platinum or other suitable compositions.

As discussed, the present method of inducing alignment markers 210 and 230 in this field will allow the repeated re-alignment of rock samples 200 using the alignment markers 210 and 230. As will be appreciated by those skilled in the art, this repeatable method will allow a faster transition in re-aligning a specific region of interest for analysis. Thus, once the alignment markers 210 and 230 are introduced on the rock sample 200, operators can remove the sample 200 from the analysis device (e.g., FIB/SEM) so the sample can be further reviewed by geologists, can be subjected to external tests or treatments (heat, chemical, etc.), and can undergo other handling. Once the sample is to be re-analyzed and imaged, operators can install the sample 200 in the same or a different analysis device (e.g., a SIMS microscope, FIB/SEM, etc.) and can realign it to the regions of interest. Navigation to the region(s) of interest can use the alignment markers 210 and 230 for dead reckoning and triangulation to the region(s) of interest. Additionally, if the analysis device has a targeting system, then the coordinates of the alignment markers 210 and 230 can be used in conjunction with the targeting system to target regions of interest.

Once a given region of interest is located, it can be analyzed using the analysis device (e.g., SIMS microscope, FIB/SEM, etc.) according to known techniques. For example, the analysis device, which can be a FIB/SEM, can successively image and remove layers of the sample in the region of interest so the imaged features can be modeled three-dimensionally for further analysis. As is known, the FIB/SEM may use a cross-beam system that can operate in three different imaging modes (SEM imaging, FIB imaging, and cross-beam imaging to monitor ion missing in real time at high resolution). Alternatively, the SIMS microscope can perform secondary ion mass spectrometry. As will be appreciated, these and other forms of analysis can be performed using any variety of analysis devices.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A method of analyzing a rock sample in one or more analysis devices, the method comprising:
    installing the rock sample in the one or more analysis devices;
    identifying a localized region of interest and a global region of interest encompassing the localized region of interest on the rock sample in the one or more analysis devices;
    performing global marking by aligning the rock sample to the global region of interest in the one or more analysis devices for marking and etching one or more global of alignment markers on the rock sample relative to the global region of interest using the one or more analysis devices; and
    performing localized marking by aligning the rock sample to the localized region of interest encompassed in the global region in the one or more analysis devices for marking and etching one or more localized of alignment markers on the rock sample relative to the localized region of interest using the one or more analysis devices.

2. The method of claim 1, wherein aligning the rock sample for marking comprises aligning the rock sample using an optical microscope as one of the one or more analysis devices.

3. The method of claim 1, wherein aligning the rock sample for marking comprises aligning the rock sample using a scanning electron microscope as one of the one or more analysis devices.

4. The method of claim 1, wherein etching the alignment markers on the rock sample comprises etching the alignment markers using a focused ion beam as one of the one or more analysis devices.

5. The method of claim 4, wherein etching the alignment markers on the rock sample comprises etching a depth of the alignment markers between 1 um and 3 um.

6. The method of claim 1, wherein etching the alignment markers on the rock sample comprises etching one or more of a vertical bar, a horizontal bar, a circle, a point, a crossed bar, a numeral, and a symbol.

7. The method of claim 1, further comprising filling the alignment markers with a material.

8. The method of claim 7, wherein the alignment markers are filled with metal.

9. The method of claim 7, further comprising polishing the rock sample.

10. The method of claim 1, wherein the alignment markers indicate a directional orientation of the rock sample.

11. The method of claim 1, further comprising removing the rock sample from the one or more analysis devices for further handling.

12. The method of claim 11, further comprising:
reinstalling the rock sample in the one or more analysis devices after further handling;
aligning the rock sample to the global region of interest in the analysis device using the one or more global alignment markers.

13. The method of claim 12, further comprising
locating the localized region of interest with the one or more global alignment markers;
aligning the rock sample to the localized region of interest with the one or more of localized alignment markers; and
analyzing the localized region of interest with the one or more analysis devices.

14. A method of analyzing a rock sample in one or more analysis devices, the method comprising:
installing the rock sample in the one or more analysis devices;
identifying a region of interest on the rock sample using the one or more analysis devices;
using the one or more analysis devices to place one or more alignment markers on the rock sample to facilitate location of the region of interest;
removing the rock sample from the one or more analysis devices for further handling;
reinstalling the rock sample in the one or more analysis devices after further handling; and
aligning the rock sample to the region of interest in the one or more analysis devices using the one or more alignment markers.

15. The method of claim 14, wherein using the one or more analysis devices to place the one or more alignment markers on the rock sample comprises placing one or more global elements and one or more local elements of the one or more alignment markers.

16. The method of claim 15, wherein the one or more local elements are contained in a local region defined by the one or more global elements.

17. The method of claim 15, wherein reinstalling the rock sample in the one or more analysis devices after further handling and aligning the rock sample to the region of interest in the one or more analysis devices using the one or more alignment markers comprises:
locating the region of interest globally with the one or more global elements;
aligning the rock sample locally to the region of interest with the one or more local elements; and
analyzing the region of interest with the one or more analysis devices.

18. The method of claim 14, wherein the one or more analysis devices comprises one or more of an optical microscope, a scanning electron microscope, and a focused ion beam.

19. The method of claim 14, wherein using the one or more analysis devices to place the one or more alignment markers on the rock sample to facilitate location of the region of interest comprises giving the one or more alignment markers with a depth between 1 -μm and 3 -μm.

20. The method of claim 14, wherein using the one or more analysis devices to place the one or more alignment markers on the rock sample to facilitate location of the region of interest comprises indicating a directional orientation of the rock sample with the one or more alignment markers.

21. The method of claim 14, wherein using the one or more analysis devices to place the one or more alignment markers on the rock sample to facilitate location of the region of interest comprises placing one or more of a vertical bar, a horizontal bar, a circle, a point, a crossed bar, a numeral, and a symbol for the one or more alignment markers.

22. The method of claim 14, wherein removing the rock sample from the one or more analysis devices for further handling comprises filling the one or more alignment markers with a material.

23. The method of claim 22, wherein the alignment markers are filled with metal.

24. The method of claim 14, wherein removing the rock sample from the one or more analysis devices for further handling comprises polishing the rock sample.

* * * * *